United States Patent [19]

Stringer et al.

[11] Patent Number: 5,417,661
[45] Date of Patent: May 23, 1995

[54] SAFETY SYRINGE

[76] Inventors: Jeffrey L. Stringer, 11700 Palm Ave., Bakersfield, Calif. 93312; Blake N. Molhook, 7307 Pembroke Ave., Bakersfield, Calif. 93308

[21] Appl. No.: 238,225

[22] Filed: May 4, 1994

[51] Int. Cl.⁶ .................................................. A61M 5/00
[52] U.S. Cl. ........................................ 604/110; 604/195
[58] Field of Search ............... 604/195, 192, 187, 110, 604/263, 218, 228

[56] References Cited

U.S. PATENT DOCUMENTS

| | | |
|---|---|---|
| 150,262 | 4/1874 | Slavin . |
| 2,034,294 | 3/1936 | Hein . |
| 4,747,830 | 5/1988 | Gloyer et al. . |
| 4,826,483 | 5/1989 | Molnar, IV . |
| 4,863,433 | 9/1989 | Payne et al. . |
| 4,888,002 | 12/1989 | Braginetz et al. . |
| 4,969,877 | 11/1990 | Kornberg ............................ 604/195 |
| 4,986,813 | 1/1991 | Blake, III et al. . |
| 4,995,870 | 2/1991 | Baskas . |
| 4,998,920 | 3/1991 | Johnson . |
| 5,019,043 | 5/1991 | Pastor et al. . |
| 5,019,045 | 5/1991 | Lee . |
| 5,135,510 | 8/1992 | Maszkiewicz et al. ............. 604/195 |
| 5,167,632 | 12/1992 | Eid et al. ......................... 604/195 X |
| 5,171,300 | 12/1992 | Blake, III et al. . |
| 5,195,985 | 3/1993 | Hall . |
| 5,222,944 | 6/1993 | Harris ................................... 604/110 |
| 5,242,419 | 9/1993 | Kiner et al. .......................... 604/195 |

*Primary Examiner*—John D. Yasko
*Attorney, Agent, or Firm*—David Weiss

[57] ABSTRACT

A disposable safety hypodermic syringe wherein the used syringe needle is rearwardly released from the syringe barrel by rotating the syringe plunger, and the needle is captured completely within the barrel when the plunger is retracted and locked with respect to the barrel.

26 Claims, 2 Drawing Sheets

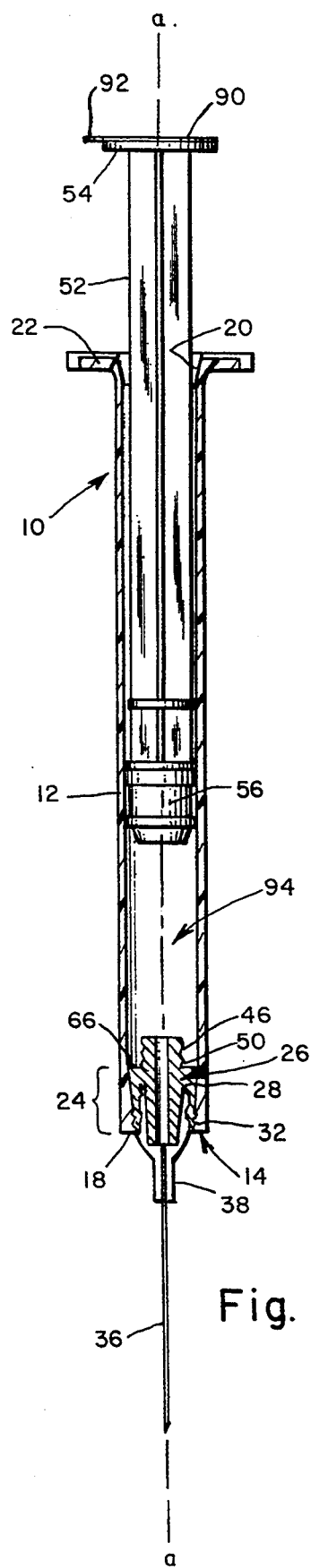
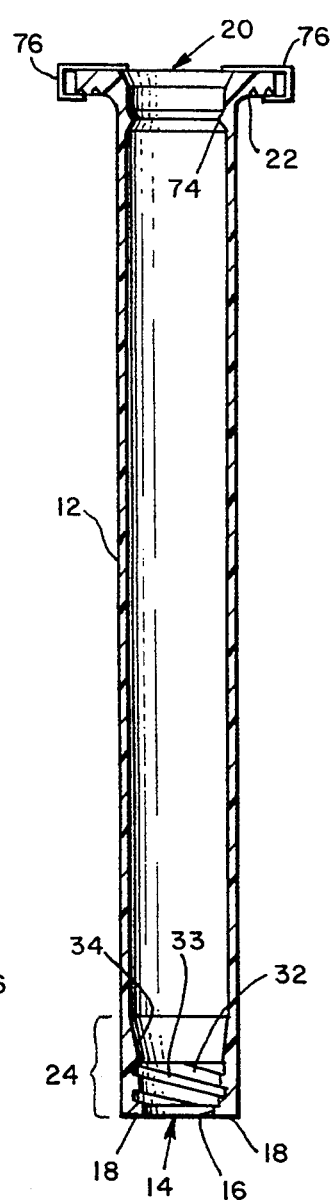
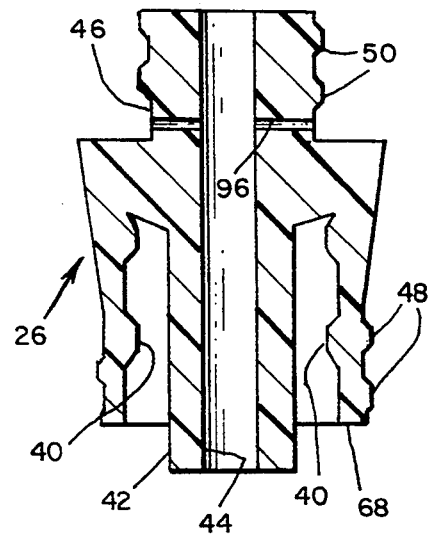
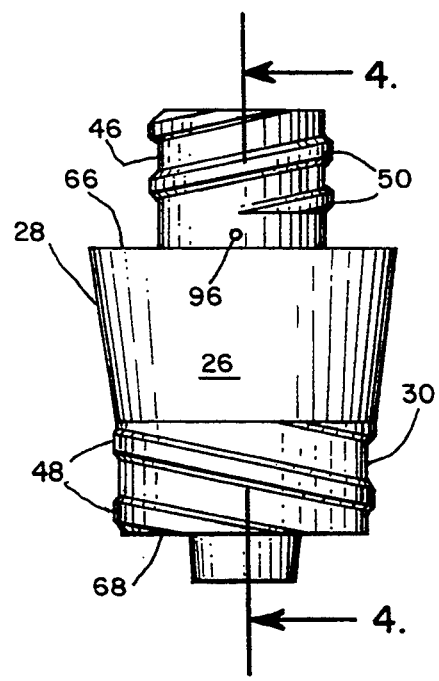
Fig. 1.
Fig. 2.
Fig. 3.
Fig. 4.

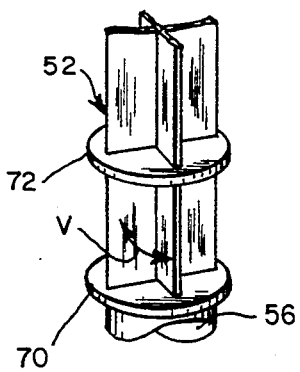
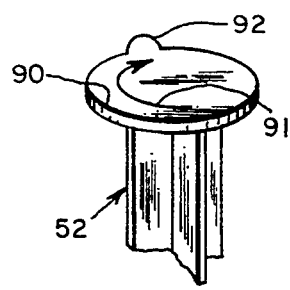
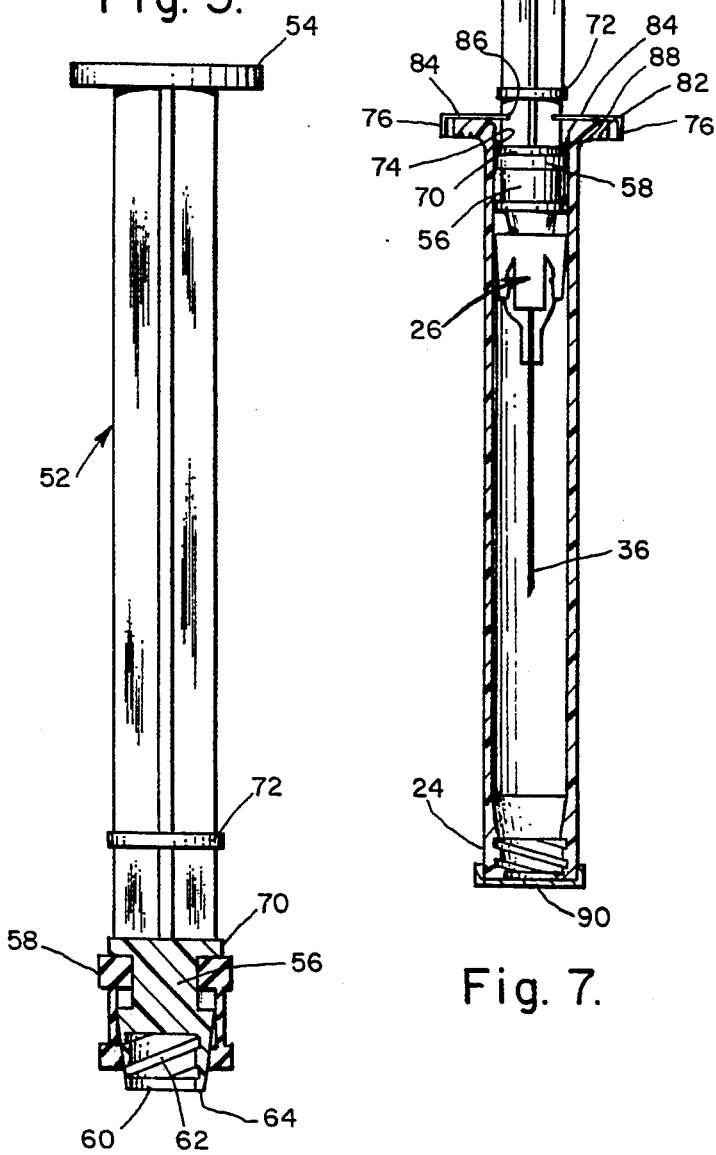
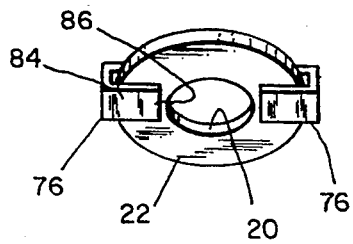
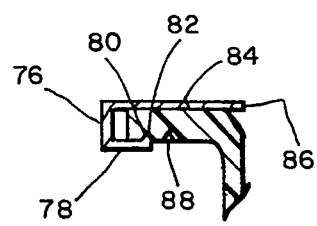

SAFETY SYRINGE

BACKGROUND OF THE INVENTION

This invention relates to hypodermic syringes, and more particularly to a syringe which may be safely disposed of and rendered inoperable after use.

It is common practice to dispose of hypodermic syringes after being used for injecting a medicinal fluid into or beneath a patient's skin, primarily for avoiding the transmission of communicable diseases through syringe reuse. After such single use, it is important to render the syringe needle inaccessible so that accidental human contact may not be made therewith.

A typical hypodermic syringe includes a hollow barrel fitted with a plunger, and a hollow needle longitudinally extending from the distal end of the barrel. One type of safety syringe permits the plunger to be secured, after use, to the needle so that the needle may be retracted into the barrel, and various means are provided for causing the needle to be captured within the barrel. The various mechanisms for implementing such operation in the past, however, are considered to be less reliable and more cumbersome than desired, and some of these safety devices are susceptible to careless manipulation which present unacceptable risks of accidental contact with the used needle.

SUMMARY OF THE INVENTION

The present invention provides an improved hypodermic syringe with increased reliability and facility to be rendered safe after use. Briefly described, the safety syringe of the present invention comprises: a barrel having a longitudinal axis and including a distal end portion and an open proximal end rearwardly of the distal end portion; a needle base member for securing a syringe needle thereto, the needle base member secured within the barrel to the barrel's distal end portion and releasable therefrom rearwardly thereof when the needle base member is rotated about the longitudinal axis in a one rotational direction; and a plunger in the barrel and securable to the needle base member, the plunger when secured to the needle base member being rotatable in the one rotational direction for rotating the needle base member about the longitudinal axis in the one rotational direction to release the needle base member from the barrel's distal end portion rearwardly thereof. The plunger is securable to the needle base member when the plunger is longitudinally engaged therewith and, preferably, rotated about the longitudinal axis in the one rotational direction. The syringe further includes locking means carried by the barrel and actuable to cooperate with the plunger for capturing the syringe needle within the barrel when the needle is secured to the needle base member and when the plunger, secured to the needle base member which has been released from the barrel's distal end portion, is retracted along the barrel with the needle disposed completely within the barrel.

A preferred embodiment of the safety syringe according to the present invention comprises: a barrel having an internally threaded longitudinal distal end portion and an open proximal end; a needle base member for securing a syringe needle thereto and including a first threaded longitudinal portion threadedly secured to the internally threaded longitudinal distal end portion of the barrel, the needle base member further including a second threaded longitudinal portion, the first threaded longitudinal portion being reversely threaded with respect to the threads of the needle base member's second threaded longitudinal portion; and a plunger in the barrel and having a threaded longitudinal portion for threadedly engaging the second threaded longitudinal portion of the needle base member to secure the plunger to the needle base member, the plunger being rotatable when secured to the needle base member for rotating the needle base member in the direction of the threads of the second longitudinal portion to disengage the needle base member from the threaded distal end portion of the barrel. The proximal end of the barrel is rearwardly of the barrel's distal end portion, the second threaded longitudinal portion of the needle base member preferably is externally threaded and extends rearwardly within the barrel, and the threaded longitudinal portion of the plunger is preferable internally threaded.

The plunger, together with the needle base member secured thereto, is retractable along the barrel when the needle base member is disengaged from the barrel's threaded distal end portion. The barrel has a length sufficient for permitting the syringe needle, which is secured to the needle base member during use, to be disposed completely within the barrel when the plunger with the needle base member secured thereto is retracted along the barrel.

The syringe of the present invention further includes locking means carried by the barrel and actuable to cooperate with the plunger for capturing the needle within the barrel when the plunger with the needle base member secured thereto is retracted along the barrel with the needle disposed completely within the barrel. The plunger includes two longitudinally spaced-apart members thereon and the locking means carried by the barrel is actuable for extending between the two longitudinally spaced members when the plunger with the needle base member secured thereto is retracted along the barrel with the needle disposed completely within the barrel. The two members on the plunger are preferably two longitudinally spaced disks or annular flanges on the plunger, and the locking means preferably includes at least one clip carried by the barrel at its proximal end and actuable for extending between the plunger's disks or annular flanges when the plunger with the needle base member secured thereto is retracted along the barrel with the needle disposed completely within the barrel.

An optional feature of the syringe according to the present invention comprises an adherent closure member, such as a sticker, removably affixed to the proximal end of the plunger, for adhering to and covering the distal end of the barrel when the needle is captured within the barrel and after removal of the closure member from the proximal end of the plunger. The adherent closure member, or sticker, includes indicia thereon indicative of the rotational direction, when the closure member is removably affixed to the proximal end of the plunger, in which the plunger should be rotated for securing the plunger to the needle base member and for disengaging the needle base member from the distal end of the barrel.

The method for safely disposing of a syringe, utilizing this optional feature, comprises the steps of: providing a syringe including a barrel having a distal end, and a plunger having a thumb rest; providing and removably affixing an adherent closure member to the thumb rest; providing and releasably securing a syringe needle to the distal end of the barrel; using the syringe; releasing the needle from the distal end of the barrel; retracting and capturing the needle within the barrel; removing the adherent closure member from the thumb rest; and adhering the closure member to the distal end of the barrel. When the provided closure member affixed to the thumb rest includes indicia thereon indicating a rotational direction, the needle releasing step includes rotating the thumb rest in the direction indicated by the indicia on the closure member affixed to the thumb rest.

BRIEF DESCRIPTION OF THE DRAWINGS

The novel features which are believed to be characteristic of the invention, together with further advantages thereof, will be better understood from the following description considered in connection with the accompanying drawings in which a preferred embodiment of the safety syringe according to the present invention is illustrated by way of example. It is to be expressly understood, however, that the drawings are for the purpose of illustration and description only and are not intended as a definition of the limits of the invention.

FIG. 1 is a side elevation view, partly in section, of a preferred embodiment of the safety syringe according to the present invention, with a syringe needle attached thereto and the plunger in a partially retracted position;

FIG. 2 is a sectional side elevation view of the syringe barrel shown in FIG. 1;

FIG. 3 is an enlarged side elevation view of the needle base member shown in FIG. 1;

FIG. 4 is a sectional view of the needle base member of FIG. 3, taken along the line 4—4 in the direction of the appended arrows;

FIG. 5 is a side elevation view, partly in section, of the plunger shown in FIG. 1;

FIG. 6 is a perspective side view of a fragment of the plunger of FIG. 5;

FIG. 7 is a side elevation view, partly in section, of the syringe of FIG. 1, with the plunger in its fully retracted position and the syringe needle captured within the barrel, and further with the optional adherent closure member in place;

FIG. 8 is an enlarged sectional side elevation view of a fragment of the barrel's finger flange with a locking clip thereon;

FIG. 9 is a perspective elevation view of the proximal end of the barrel with a pair of oppositely disposed locking clips thereon; and FIG. 10 is a perspective view of a fragment of the plunger in the vicinity of its proximal end, showing the adherent closure member removably affixed thereto.

DESCRIPTION OF THE PREFERRED EMBODIMENT

A preferred embodiment of the assembled syringe 10 is shown in FIG. 1, and includes a hollow cylindrical barrel 12 having a longitudinal axis a-a. The barrel 12, shown in greater detail in FIG. 2, includes a distal end 14 having an aperture 16 therethrough leaving an annular end wall 18. The barrel 12 further includes an open proximal end 20 rearwardly of the barrel's distal end, and having a finger flange 22 thereat.

A longitudinal section 24 of the barrel 12, rearwardly extending from the annular distal end wall 18, has an internal surface configuration for accommodating a needle base member 26 shown in greater detail in FIG. 3 and 4. The needle base member 26 includes a beveled or conical mid-section 28 of forwardly decreasing diameter, and a first threaded longitudinal portion 30 forwardly of the beveled mid-section 28 and having a diameter approximately the same as the small diameter of the conical mid-section 28 but greater than the diameter of the aperture 16 in the distal end wall 18 of the barrel 12. The barrel's longitudinal distal end section 24 includes an internally threaded portion 32 forwardly of an internally sloped or beveled portion 34 of the longitudinal distal end section 24 of the barrel 12. The needle base member 26 is secured to the longitudinal end section 24 of the barrel 12 with the needle base member's first threaded longitudinal distal end portion 30 threadably engaging and secured to the barrel's internally threaded distal end portion 32; the sloped or beveled surfaces 28, 34 of the needle base member 26 and the barrel's longitudinal distal end section 24 are in contact and fluid-tight engagement.

When the needle base member 26 is secured to the longitudinal distal end portion 30 of the barrel 12, a conventional syringe needle assembly, including a hollow syringe needle 36 secured to a needle hub 38, may be secured to the needle base member 26 by threadably engaging the conventional externally threaded needle hub 38 with cooperating internal threads 40 of the needle base member 26 (see FIGS. 1 and 4). The needle hub 38 is thereby secured about a longitudinally extending central portion 42 of the needle base member 26 protruding through the aperture 16 of the barrel's distal end wall 18, with the hollow needle 36 communicating with the interior of the barrel 12 through a bore 44 longitudinally extending through the needle base member 26.

The needle base member 26 further includes a second threaded longitudinal portion 46, concentric with but of smaller diameter than the first threaded longitudinal portion 30. The second threaded portion 46 is preferably externally threaded and extends rearwardly within the barrel 12. The first threaded longitudinal portion 30 (and, accordingly, the barrel's internally threaded distal end portion 32) are reversely threaded with respect to the threads 50 of the second threaded longitudinal portion 46. In the example shown in FIG. 3, the external threads 50 of the second threaded portion 46 are "right-handed," and the external threads 48 of the first threaded longitudinal portion 30 (and the threads 33 of the barrel's internally threaded distal end portion 32) are "left-handed."

The syringe 12 of FIG. 1 includes a plunger 52 longitudinally extending within the barrel 12. The plunger 52, shown in greater detail in FIG. 5, is preferably cruciform in cross section and includes a thumb rest or handle 54 at its proximal end. The plunger's distal end includes a piston 56 having a compression seal (fabricated of such material as rubber) fitted thereabout for providing a fluid-tight slideable seal with the barrel 12.

The piston 56 includes a forwardly open cavity 60 therein about the longitudinal axis a-a and having internal threads 62 for threadedly engaging the second longitudinal threaded portion 46 of the needle base member 26 when the plunger 52 is forwardly moved along the longitudinal axis a-a and rotated in the direction of the cooperating threads 62, 50 (i.e. by a user rotating the plunger's thumb rest 54 in the clockwise direction while longitudinally moving the plunger 52 downwardly as viewed in the drawing of FIG. 1). The second longitudinal portion 46 of the needle base member 26 will be threadedly received by the internally threaded longitudinal portion of the plunger's distal end 60, until continued forward longitudinal or axial movement of the plunger 52 is prevented such as by the forward annular tip 64 of the plunger 56 contacting the rearwardly facing annular shoulder 66 of the needle base member's mid-section 28. The needle base member 26, of course, is constrained against forward longitudinal or axial movement by the bevel 34 of the barrel's longitudinal distal end portion 24 in contact engagement with the needle base member's beveled mid-section 28, as well as by any contact which may be made between the forward annular tip 68 of the needle base member 26 and the rearwardly facing surface of the annular end wall 18 at the distal end 14 of the barrel 12 (FIGS. 1 and 4).

Further or continued rotation of the plunger 52 in the same rotational direction (i.e. clockwise as viewed in the drawing of FIG. 1) will cause the needle base member 26, which is longitudinally secured thereto, to rotate along with the plunger 52 (i.e. in the clockwise direction as viewed in the drawing of FIG. 1). Since the externally threaded first longitudinal portion 30 of the needle base member 26 and the internally threaded portion 32 of the barrel's longitudinal distal end portion 24 are reversely threaded with respect to the threads 50 of the second longitudinal threaded portion 46 of the needle base member 26 and the internal threads 62 of the piston 56 at the forward end of the plunger 52, such rotation of the needle base member 26 will cause the needle base member's first threaded longitudinal portion 30 to threadedly disengage rearwardly from the barrel's internally threaded portion 32. Such rearward disengagement will cause the needle base member 26 with the syringe needle 36 secured thereto to be released from its securement with the distal end portion 24 of the barrel 12. Further rearward longitudinal movement of the plunger 52 will then cause the needle base member 26 with the secured needle 36 to be retracted into the barrel 12 as shown in FIG. 7.

Preferably the number of threads 48, 50 are within a range for effecting securement of the plunger 52 to the needle base member 26 by rotating the plunger about one-half turn, and for effecting disengagement of the needle base member 26 from the barrel distal end portion 24 by a further approximately one-half turn of the plunger 52—for example, approximately 1½ thread revolutions.

As shown in FIGS. 5, 6 and 7, the plunger 52 includes two longitudinally spaced-apart members 70, 72 thereon in the vicinity of the plunger's distal end. The members 70, 72 may be radially oriented walls or disks when viewed with the cruciform structure of the plunger 52, the outer or circumferential portions thereof forming annular flanges. The forwardmost disk or flange 70 is preferably a part of and comprises the rear portion or wall of the plunger piston 56. An inwardly extending annular protrusion 74 on the internal surface of the barrel 12 near its open proximal end 20 is useful for signaling the user to cease withdrawing the plunger 52 from the barrel 12 when resistance to further rearward movement of the plunger 52 is felt upon either of the flanges 72, 70 contacting the protrusion 74. Alternatively, the flange or disk 72 may have a smaller diameter than the flange or disk 70 so that the flange 72 may easily pass by the protrusion 74 while the flange 70 will provide greater resistance to continued rearward movement of the plunger 52. A further alternative would have the diameters of both flanges 70, 72 sufficiently small for easily passing by the protrusion 74, in which case the stopping signal will be initiated by the compression seal 58 contacting the protrusion 74. In any event, the barrel 12 is sufficiently long such that the syringe needle 36 is completely disposed within the barrel 12 when the plunger 52 is withdrawn to its fully extended position with the plunger piston 56 remaining within the barrel 12 in the vicinity of the barrel's open proximal end 20.

As best shown in FIGS. 2, 8 and 9, the finger flange 54 at the proximal end 20 of the barrel 12 has at least one and preferably a pair of locking members or clips 76. Referring particularly to FIG. 8, the forward shorter leg 78 of each U-shaped clip 76 includes a protrusion or detent 80 normally positioned in an outer groove 82 on the finger flange 22 such that the clip 76 is in a first radial position (in respect of the barrel's longitudinal axis a-a) with the clip's rearward longer leg 84 radially disposed with its free edge or tip 86 not extending into or covering the opening at the barrel's open proximal end 20 so that the leg 84 does not interfere with movement of the plunger 52. The two clips 76, which preferably extend aligned with each other and a diameter of the barrel 12, may be radially urged toward the longitudinal axis a-a, upon which occurrence the detent 80 is released from the outer grove 82 of the finger flange 22 and engages an inner grove 88 of the finger flange 22 (see also FIG. 7). When the clip 76 is so actuated, the clip's rearward leg 84 moves toward the barrel's longitudinal axis a-a and partially covers the barrel opening 20. The plunger 52 preferably has been rotated such that the tip 86 of the clip's rearward leg 84 extends within one of the 90 degree sectors of the plunger cruciform, and in any event the leg 84 extends between the longitudinally spaced-apart disks or flanges 70, 72. The clips 76 are locked in this position once actuated, by the clips' detents 80 being captured by the respective inner grooves 88 of the finger flange 22. It may be appreciated that the clips 76, when so actuated to extend between the flanges 70, 72, prevent longitudinal movement of the plunger 52 with respect to the barrel 12 greater than the separation between the two flanges 70, 72, thereby effectively locking the plunger 52 and capturing the needle 36 disposed completely within the barrel 12.

Turning to FIG. 10, there is shown an optional feature of the safety syringe 10 according to the present invention, in which an adherent flexible sheet member 90, such as a sticker, is removably affixed to the proximal end or thumb rest 54 of the plunger 52, and includes thereon indicia such as an arrow 91 indicative of the rotational direction in which the plunger 52 should be rotated for releasing the needle base member 26 to permit the needle 36 to be retracted into the barrel 12. After the syringe 10 is "made safe" by capturing the needle 36 within the barrel 12, the sticker 90 may be peeled or otherwise removed from the thumb rest 54 and then used to cover the aperture 16 at the barrel's distal end 14 by adhering the sticker 90 thereto. The diameter of the sticker 90 is preferably greater than the diameter of the barrel 12 and somewhat pliable, so that the sticker 90 may slightly overlap and adhere to the longitudinal outer surface of the barrel's distal end portion 24 as shown in FIG. 7. The sticker 90 may include a tab 92 (FIG. 10) for facilitating removal of the sticker 90 from the plunger's thumb rest 54 and its installation onto the barrel's distal end 14.

A user, when utilizing the safety syringe 10 of the present invention, affixes the conventional syringe needle assembly 36, 38 to the needle base member 26 as shown in FIG. 1. The chamber 94 forwardly of the plunger piston 56 is filled with medicinal fluid in conventional manner, and the syringe is used to inject the fluid into the patient. After such injection or use, the user pushes the plunger 52 longitudinally within the barrel 12 (i.e. downwardly viewed in the drawing of FIG. 1) while rotating the plunger's thumb rest or handle 54 in the rotational direction of the threads 50, 62, as indicated on the thumb rest sticker 90, i.e. in the clockwise direction for the syringe embodiment shown in the drawing. Pressure build-up of any remaining fluid in the passageway 44 of the needle base member 26 will be relieved through radial aperture 96 (FIGS. 3 and 4). After the plunger piston 54 threadedly engages the needle base member 26 and is secured thereto, further clockwise rotation of the plunger thumb rest or handle 54 will cause the needle base member 26 to rearwardly threadedly disengage (i.e. upwardly as viewed in FIG. 1) from the longitudinal distal end portion 32 of the barrel 12 and to be released therefrom.

The user then rearwardly pulls the plunger thumb rest or handle 54 (i.e. upwardly as viewed in FIG. 1), causing the plunger 52 with the secured needle base member 26 to rearwardly move along the barrel's longitudinal axis until the user is signaled to cease pulling the thumb rest 54 by the flange 72 or the flange 70 or the compression seal 58 engaging the barrel's internal protrusion 74 near the barrel's open proximal end 20. In any event, the user assures that the flange 72 is positioned just rearwardly of the finger flange 22 of the barrel 52, as shown in FIG. 7, whereupon the user urges the locking clips 76 radially inwardly, slightly rotating the thumb rest 54 if necessary to assure that the clips' rearward legs 84 enter a 90 degree sector or "V" of the cruciform plunger 52 (i.e. if the plunger 52 is of a cruciform cross-section). The locking clips 76 are thereupon locked in this position by the detents 80 being captured in their respective inner grooves 88 in the finger flange 22, the clips' rearward legs 84 extending between the two disks or annular flanges 70, 72 and preventing longitudinal movement of the plunger 52 greater than the distance between the two flanges 70, 72. The needle 36, which has been retracted completely into the barrel 12, is thus locked in place within the barrel 12. In addition, rotation of the cruciform plunger 52 is prevented or restricted by the presence of the clips' rearward legs 84 within respective sectors or V's of the plunger 52.

If desired, and for preventing any remaining medicinal fluid from leaking through the aperture 16 at the barrel's distal end, the sticker 90 may be removed from the thumb rest 54, and placed upon and adhered to the distal end of the barrel 12 to close the aperture 16 thereat. Such stickers or adherent closure members 90 are preferably of the pressure sensitive adherent type.

The barrel 12, the plunger 54 with its threaded forward end 56 and its disks or annular flanges 70, 72, and the needle base member 26, may be molded parts of plastic materials, for example polyethylene.

Thus there has been described a preferred embodiment of an improved safety syringe which is easy to use for reliably locking or capturing the syringe needle completely within the syringe barrel immediately after the syringe has been used, and for further closing the syringe barrel's open distal end after the needle has been captured. Other embodiments of the syringe of the present invention, and modifications of the preferred embodiment shown herein, may be developed without departing from the essential characteristics of the invention. Accordingly, the invention should be limited only by the scope of the claims listed below.

We claim:

1. A safety syringe, comprising:
   a syringe needle assembly including a needle hub and a syringe needle secured to said hub;
   a barrel having an aperture at its distal end for receiving said needle hub, an internally threaded longitudinal distal end portion and an open proximal end;
   a needle base member for securing said syringe needle assembly thereto when said hub is received by said aperture, said needle base member including a first threaded longitudinal portion threadedly secured to said internally threaded distal end portion of said barrel, said needle base member further including a second threaded longitudinal portion, said first threaded longitudinal portion being reversely threaded with respect to the threads of said second threaded longitudinal portion; and
   a plunger in said barrel and having a threaded longitudinal portion for threadedly engaging said second threaded longitudinal portion of said needle base member to secure said plunger to said needle base member, said plunger being rotatable when secured to said needle base member for rotating said needle base member in the direction of the threads of said second threaded longitudinal portion to disengage said needle base member from said threaded distal end portion of said barrel.

2. The syringe according to claim 1, wherein:
   said proximal end of said barrel is rearwardly of said distal end portion of said barrel;
   said second threaded longitudinal portion of said needle base member is externally threaded and extends rearwardly within said barrel; and
   said threaded longitudinal portion of said plunger is internally threaded.

3. The syringe according to claim 1, wherein:
   said plunger with said needle base member secured thereto is retractable along said barrel when said needle base member is disengaged from said threaded distal end portion of said barrel.

4. The syringe according to claim 3, wherein:
   said syringe needle assembly is secured to said needle base member, and
   said barrel has a length sufficient for permitting said needle to be disposed completely within said barrel when said plunger with said needle base member secured thereto is retracted along said barrel.

5. The syringe according to claim 4, further including:
   locking means carried by said barrel and actuable to cooperate with said plunger for capturing said needle within said barrel when said plunger with said needle base member secured thereto is retracted along said barrel with said needle disposed completely within said barrel.

6. The syringe according to claim 4, further including:
   two longitudinally spaced members on said plunger; and
   locking means on said barrel and actuable for extending between said two longitudinally spaced members when said plunger with said needle base member secured thereto is retracted along said barrel with said needle disposed completely within said barrel.

7. The syringe according to claim 6, wherein:

said locking means is carried by said barrel in the vicinity of said proximal end.

8. The syringe according to claim 4, further including:
two longitudinally spaced annular flanges on said plunger; and
at least one clip carried by said barrel at said proximal end and actuable for extending between said annular flanges when said plunger with said needle base member secured thereto is retracted along said barrel with said needle disposed completely within said barrel.

9. The syringe according to claim 3, further including:
locking means carried by said barrel and actuable to cooperate with said plunger for capturing the syringe needle within said barrel when the needle is secured to said needle base member and said plunger with said needle base member secured thereto is retracted along said barrel with the needle disposed completely within said barrel.

10. The syringe according to claim 3, further including:
two longitudinally spaced members on said plunger; and
locking means on said barrel and actuable for extending between said two longitudinally spaced members when said plunger with said needle base member secured thereto is retracted along said barrel with the syringe needle, when secured to said needle base member, disposed completely within said barrel.

11. The syringe according to claim 10, wherein:
said two longitudinally spaced members include longitudinally spaced annular flanges on said plunger; and
said locking means includes at least one clip carried by said barrel in the vicinity of said proximal end.

12. The syringe according to claim 9, further including:
an adherent closure member for adhering to and covering the distal end of said barrel when the syringe needle is captured within said barrel.

13. The syringe according to claim 9, wherein said plunger includes a proximal end, and further including an adherent closure member removably affixed to said proximal end of said plunger, for adhering to and covering the distal end of said barrel after removal of said closure member from the proximal end of said plunger.

14. The syringe according to claim 13, wherein:
said closure member affixed to said proximal end of said plunger includes indicia thereon indicative of the direction for rotating said plunger to secure said needle base member thereto and to disengage said needle base member from said distal end portion of said barrel.

15. In a method for safely disposing of a syringe, the steps comprising:
providing a syringe including a barrel having a distal end, and a plunger having a thumb rest;
providing and removably affixing an adherent closure member to said thumb rest;
providing and releasably securing a syringe needle to said distal end of said barrel;
using said syringe;
releasing said needle from said distal end of said barrel;
retracting and capturing said needle completely within said barrel;
removing said adherent closure member from said thumb rest; and
adhering said adherent closure member to said distal end of said barrel.

16. The method according to claim 15, wherein:
said adherent closure member affixed to said thumb rest includes indicia thereon indicating a rotational direction; and
during said needle releasing step, rotating said thumb rest in the rotational direction indicated by said indicia on said adherent closure member.

17. A safety syringe, comprising:
a barrel having a longitudinal axis and including a distal end portion and an open proximal end rearwardly of said distal end portion;
a needle base member for securing a syringe needle thereto, said needle base member secured within said barrel to said distal end portion and releasable therefrom rearwardly thereof when said needle base member is rotated about said longitudinal axis in a one rotational direction;
a plunger in said barrel and securable to said needle base member when longitudinally engaged therewith and rotated about said longitudinal axis in said one direction, said plunger when secured to said needle base member being rotatable in said one rotational direction for rotating said needle base member about said longitudinal axis in said one rotational direction to release said needle base member from said distal end portion rearwardly thereof;
two longitudinally spaced members on said plunger; and
locking means on said barrel and actuable for extending between said two longitudinally spaced members when said plunger, secured to said needle base member released from said distal end portion, is retracted along said barrel with the syringe needle, when secured to said needle base member, disposed completely within said barrel.

18. The syringe according to claim 17, wherein:
said two longitudinally spaced members include two longitudinally spaced annular flanges on said plunger; and
said locking means includes at least one clip carried by said barrel in the vicinity of said proximal end.

19. A safety syringe, comprising:
a barrel having a longitudinal axis and including a distal end portion and an open proximal end rearwardly of said distal end portion;
a needle base member for securing a syringe needle thereto, said needle base member secured within said barrel to said distal end portion and releasable therefrom rearwardly thereof when said needle base member is rotated about said longitudinal axis in a one rotational direction;
a plunger in said barrel and including a proximal end, said plunger securable to said needle base member, said plunger when secured to said needle base member being rotatable in said one rotational direction for rotating said needle base member about said longitudinal axis in said one rotational direction to release said needle base member from said distal end portion rearwardly thereof;
locking means carried by said barrel and actuable to cooperate with said plunger for capturing the syringe needle within said barrel when the needle is secured to said needle base member and when said plunger, secured to said needle base member released from said distal end portion, is retracted along such barrel with the needle disposed completely within said barrel; and an adherent closure member removably affixed to said proximal end of said plunger, for adhering to and covering the distal end of said barrel when the needle is captured within said barrel and after removal of said closure member from said proximal end of said plunger.

20. The syringe according to claim 19, wherein: said closure member affixed to said proximal end of said plunger includes indicia thereon indicative of said one rotational direction.

21. A safety syringe, comprising:
a barrel having a distal end and a proximal end;
a syringe needle releasably secured to said barrel at said distal end;
a plunger in said barrel and securable to said needle for releasing said needle from said distal end of said barrel, said plunger with said needle secured thereto being retractable along said barrel when said needle is released from said distal end of said barrel;
two longitudinally spaced members on said plunger; and
locking means carried by said barrel and actuable for extending between said two longitudinally spaced members for capturing said needle within said barrel when said plunger with said needle secured thereto is retracted along said barrel with said needle disposed completely within said barrel.

22. The syringe according to claim 21, said locking means is carried on said barrel in the vicinity of said proximal end.

23. The syringe according to claim 21, further including:

an adherent closure member for adhering to and covering said distal end of said barrel when said syringe needle is captured within said barrel.

24. The safety syringe according to claim 21, wherein:
said two longitudinally spaced members include two longitudinally spaced annular flanges on said plunger; and
said locking means includes at least one clip carried by said barrel at said proximal end.

25. A safety syringe, comprising:
a barrel having a distal end and a proximal end;
a syringe needle releasably secured to said barrel at said distal end;
a plunger in said barrel and including a proximal end, said plunger securable to said needle for releasing said needle from said distal end of said barrel, said plunger with said needle secured thereto being retractable along said barrel when said needle is released from said distal end of said barrel;
locking means carried by said barrel and actuable to cooperate with said plunger for capturing said needle within said barrel when said plunger with said needle secured thereto is retracted along said barrel when said needle is disposed completely within said barrel; and
an adherent closure member removably affixed to said proximal end of said plunger, for adhering to and covering said distal end of said barrel when said needle is captured within said barrel and after removal of said closure member from said proximal end of said plunger.

26. The syringe according to claim 25, wherein:
said plunger is rotatable in a one rotational direction for releasing said needle from said distal end of said barrel; and
said closure member affixed to said proximal end of said plunger includes indicia thereon indicative of said one rotational direction.

* * * * *